United States Patent
Van Der Zee

(10) Patent No.: US 11,602,297 B2
(45) Date of Patent: Mar. 14, 2023

(54) DEVICE FOR RECORDING A MULTI-CHANNEL-ECG AND A METHOD THERE FOR

(71) Applicant: STICHTING CARDIOVASCULAIRE BIOLOGIE (SCB), Delft (NL)

(72) Inventor: Marinus Cornelis Van Der Zee, Delft (NL)

(73) Assignee: STICHTING CARDIOVASCULAIRE BIOLOGIE (SCB), Delft (NL)

( * ) Notice: Subject to any disclaimer, the term of this patent is extended or adjusted under 35 U.S.C. 154(b) by 0 days.

(21) Appl. No.: 16/973,858

(22) PCT Filed: Jun. 11, 2019

(86) PCT No.: PCT/NL2019/050351
§ 371 (c)(1),
(2) Date: Dec. 10, 2020

(87) PCT Pub. No.: WO2019/240573
PCT Pub. Date: Dec. 19, 2019

(65) Prior Publication Data
US 2021/0259612 A1    Aug. 26, 2021

(30) Foreign Application Priority Data
Jun. 13, 2018    (NL) ...................................... 2021115

(51) Int. Cl.
*A61B 5/333*    (2021.01)
*A61B 5/332*    (2021.01)
(Continued)

(52) U.S. Cl.
CPC .............. *A61B 5/333* (2021.01); *A61B 5/265* (2021.01); *A61B 5/283* (2021.01); *A61B 5/332* (2021.01);
(Continued)

(58) Field of Classification Search
CPC ................................. A61B 5/332; A61B 5/333
See application file for complete search history.

(56) References Cited

U.S. PATENT DOCUMENTS 3,830,227 A * 8/1974 Green .................... A61B 5/332
   600/514
4,295,474 A * 10/1981 Fischell ................. A61B 5/333
   600/510
(Continued)

FOREIGN PATENT DOCUMENTS

DE    102005036501 A1    2/2007
DE    202016105433 U1    11/2016
(Continued)

OTHER PUBLICATIONS

International Search Report and Written Opinion for the International Patent Application No. PCT/NL2019/050351, dated Aug. 20, 2019, 16 pages.

*Primary Examiner* — George R Evanisko
(74) *Attorney, Agent, or Firm* — KDB Firm PLLC

(57) ABSTRACT

A device, an electrode and method for recording a multi-channel-ECG. The device includes a housing; a processor configured to record a multi-channel-ECG; at least two electrodes that can be operatively connected with the processor; and a connection module configured to connect the at least two electrodes and/or processor with a data processing element. The device is configured to be handheld.

18 Claims, 9 Drawing Sheets

(51) Int. Cl.
*A61B 5/339* (2021.01)
*A61B 5/265* (2021.01)
*A61B 5/283* (2021.01)
*A61B 5/00* (2006.01)

(52) U.S. Cl.
CPC .............. *A61B 5/339* (2021.01); *A61B 5/746* (2013.01); *A61B 2560/0214* (2013.01); *A61B 2562/0215* (2017.08)

(56) References Cited

U.S. PATENT DOCUMENTS

| | | | |
|---|---|---|---|
| 5,511,553 A * | 4/1996 | Segalowitz | A61B 5/282 600/508 |
| 2007/0208262 A1* | 9/2007 | Kovacs | A61B 5/333 600/509 |
| 2010/0174204 A1* | 7/2010 | Danteny | A61B 5/332 600/509 |

FOREIGN PATENT DOCUMENTS

| | | |
|---|---|---|
| FR | 2666977 A1 | 3/1992 |
| FR | 2917961 A1 | 1/2009 |
| WO | 0041620 A1 | 7/2000 |

* cited by examiner

Figure 7:
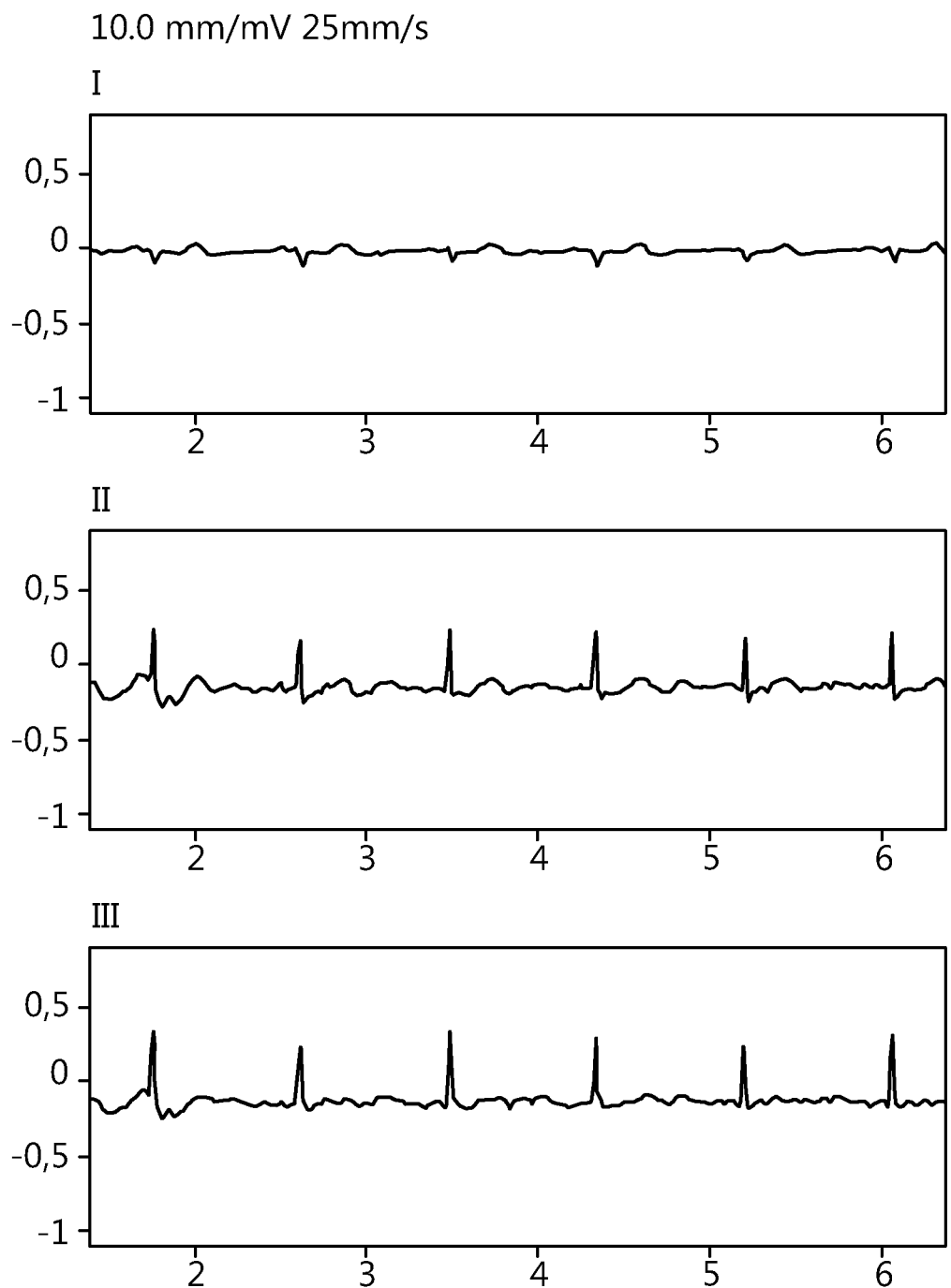
Figure 7:
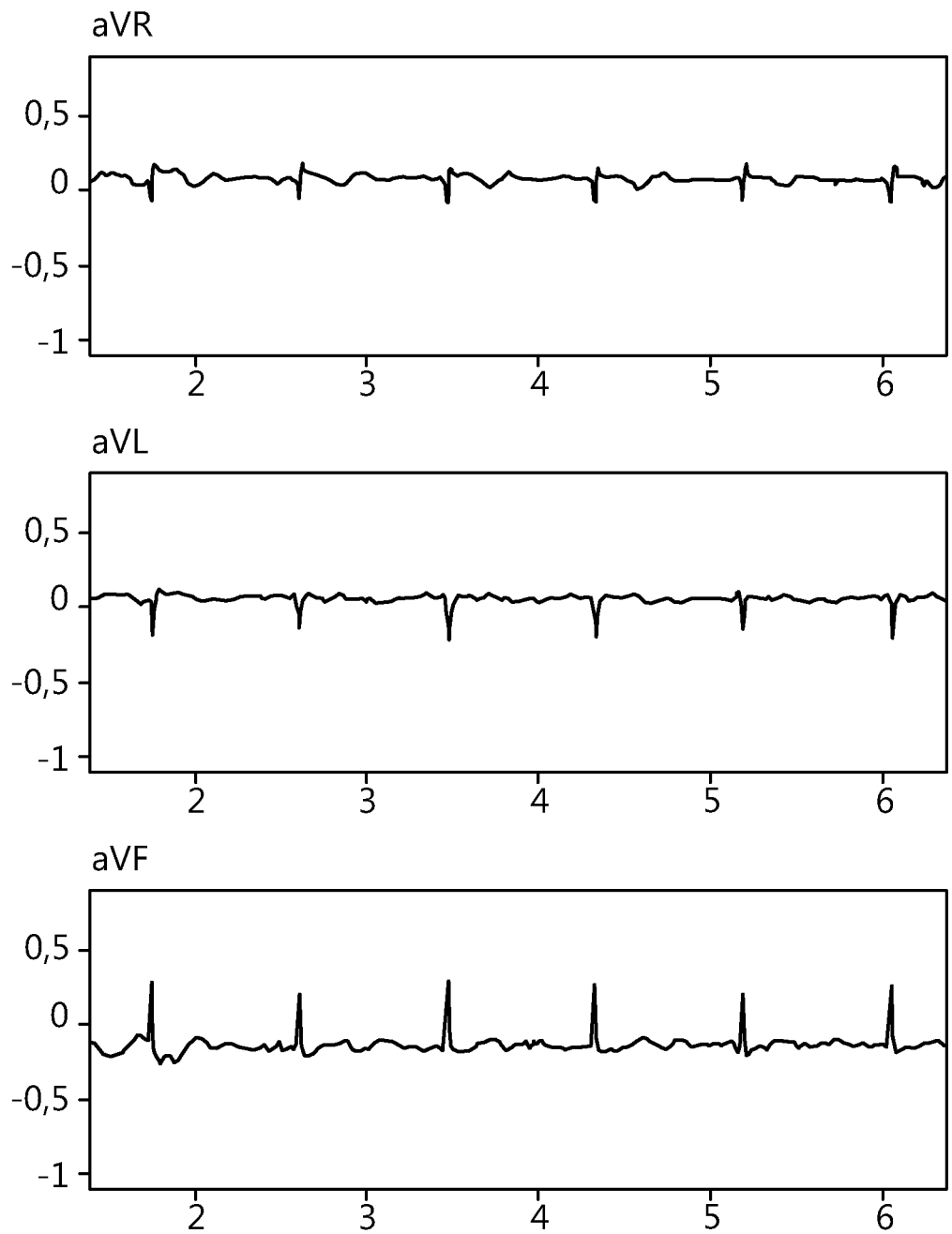

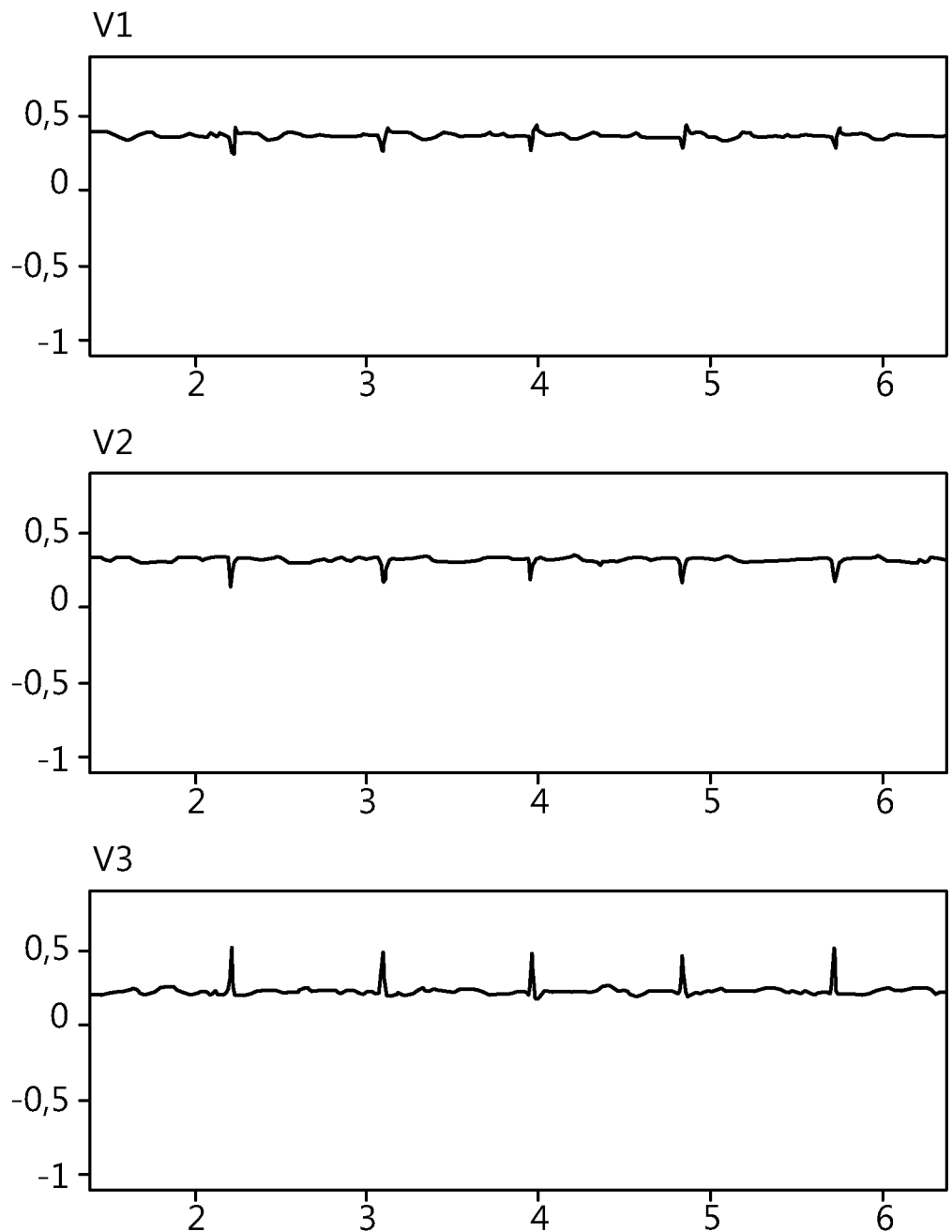
Fig. 7 end

Figure 8:
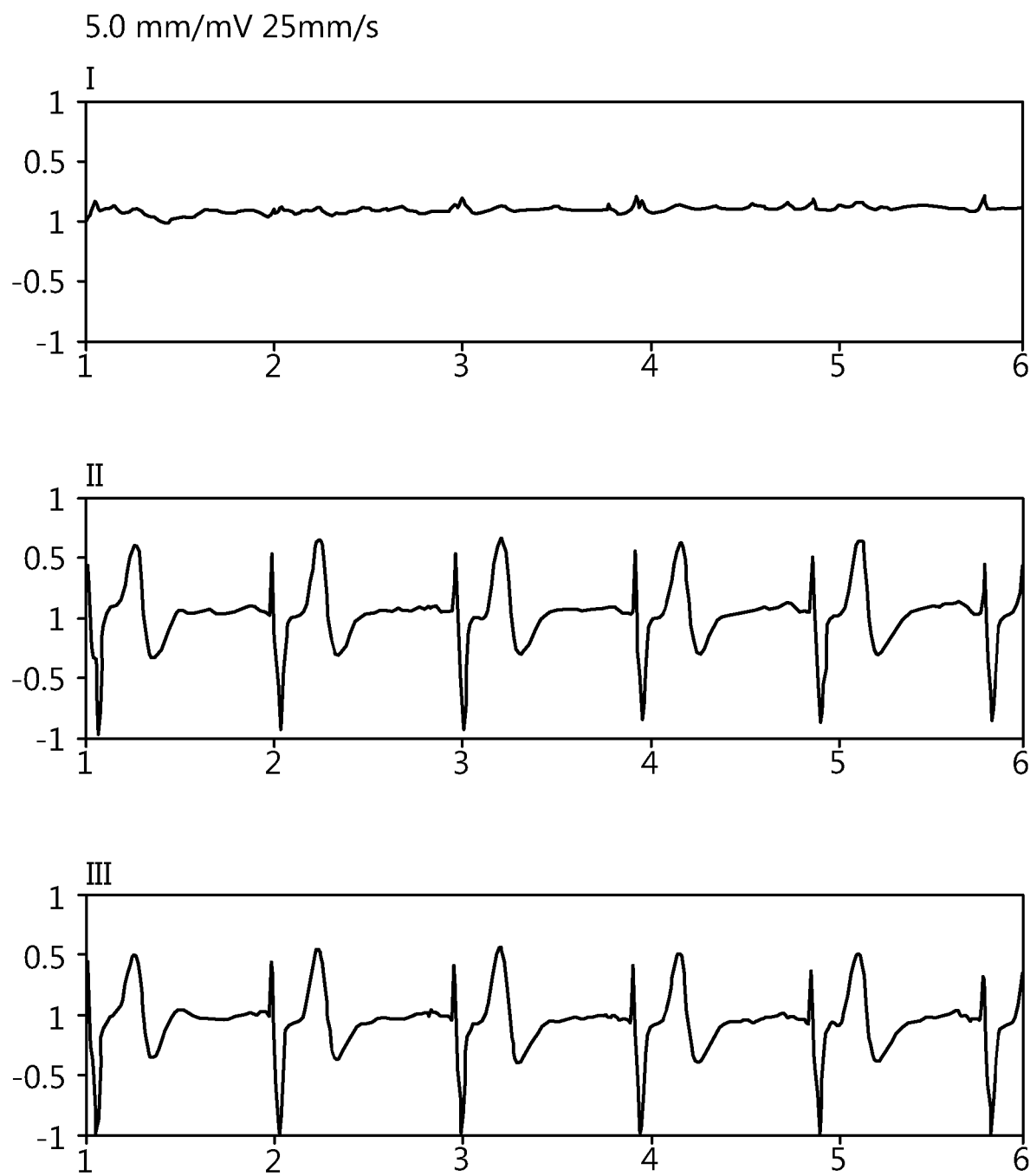
Figure 8:
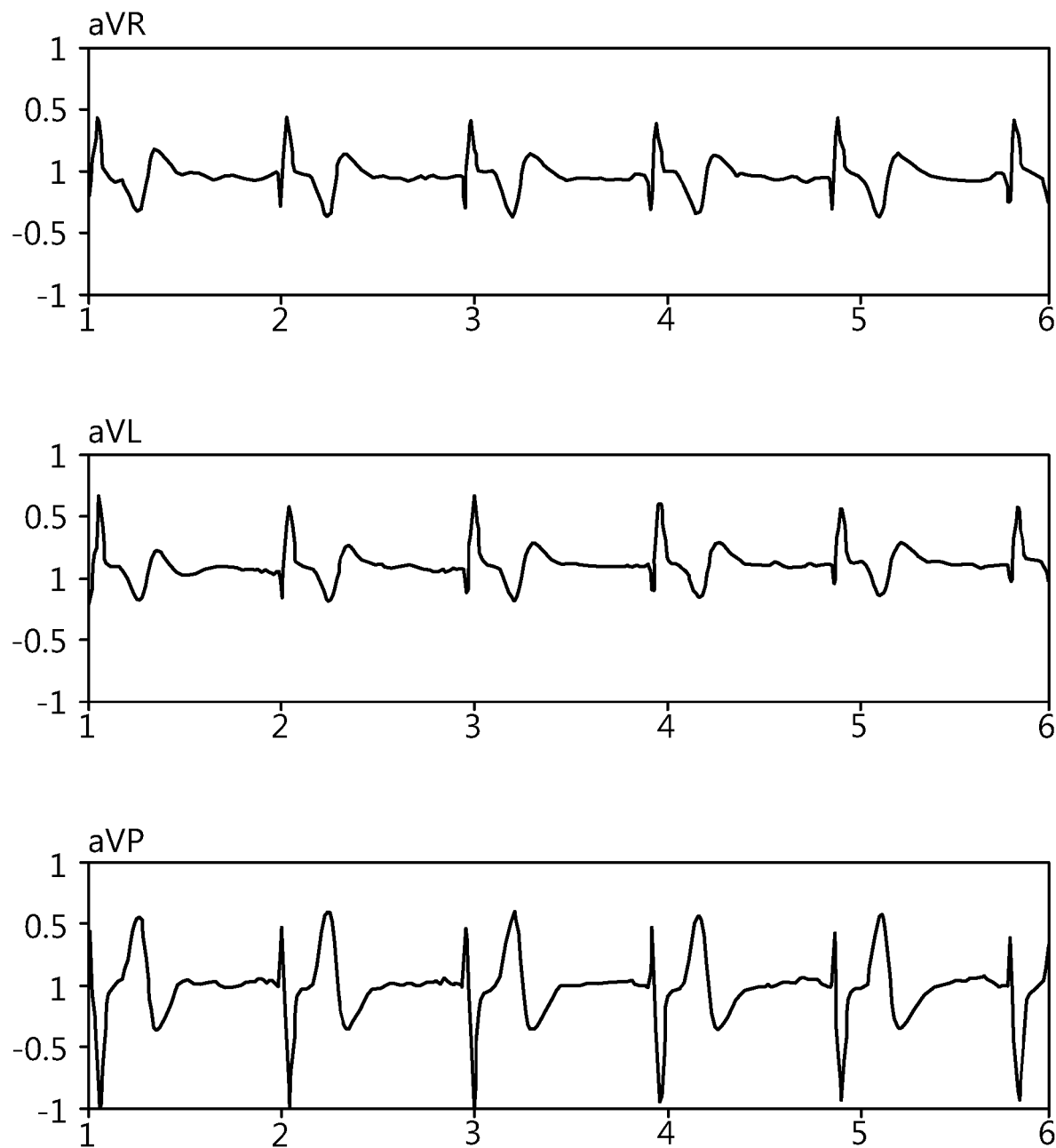

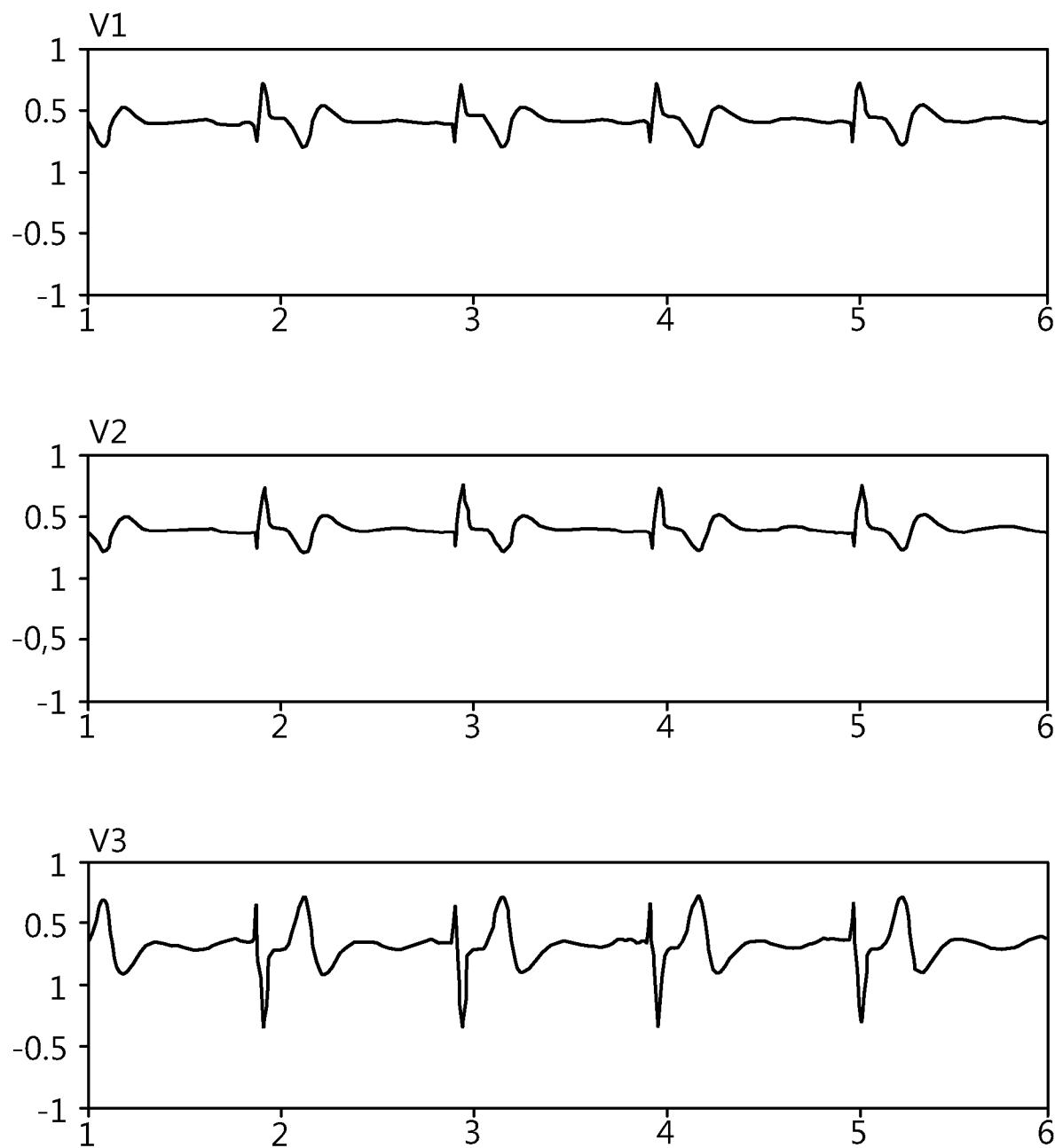
Fig. 8 end

DEVICE FOR RECORDING A MULTI-CHANNEL-ECG AND A METHOD THERE FOR

This is a national stage application filed under 35 U.S.C. § 371 of pending international application PCT/NL2019/050351, filed Jun. 11, 2019, which claims priority to Netherlands Patent Application No. 2021115, filed Jun. 13, 2018, the entirety of which applications are hereby incorporated by reference herein.

The invention relates to a device for recording a multi-channel-electrocardiogram (multi-channel-ECG). More specifically, the recording of multi-channel-ECG relates to obtaining a meaningful ECG and the prevention of health damage.

A heart generates an electric pulse which causes the heart to pump and circulate blood through the blood vessels. Due to the electrical pulses an electrical field is generated that can be detected by electrodes. These electrodes are positioned on or inside the body.

Conventional devices for recording multi-channel-ECG involve the use of large equipment and require an operator to operate, perform and analyse multi-channel-ECG. Such process is labour intensive and requires substantial financial investments in equipment and people. For example, ten electrodes are positioned on the body, in general one electrode on each of the limbs and six electrodes at specific places on the chest. This approach will then result in a 12-channel-ECG which shows the electrical activities of the heart in a frontal, sagittal and/or horizontal plane. Typically, this process of performing a conventional ECG takes several minutes.

An objective of the present invention is to provide a device for recording a multi-channel-ECG that obviates or at least reduces the aforementioned problems.

This object is achieved with a device for recording a multi-channel-ECG according to the invention, the device comprising:
- a housing;
- a processor configured to record a multi-channel-ECG;
- at least two electrodes that can be operatively connected with the processor; and
- a connection module configured to connect the at least two electrodes and/or processor with a data processing element, wherein the device is configured to be handheld.

The connection module can be positioned inside and/or outside of the housing in order to be able to be connected with another device. In the context of the invention handheld means a device with dimensions such that a user would be capable to carry and/or hold the device in his or her hand.

Providing a handheld device enables effective, fast and efficient analyses without requiring many complex operations. This significantly reduces the financial investments in equipment and/or people.

Another advantage is that the effective, fast and efficient analysis enables a user or patient to self-monitor his or her condition. In view of the fact that coronary diseases and/or coronary malfunctioning are an ever growing problem in society, the device according to the invention provides the advantage that health problems can be detected at an earlier stage. As such, the device according to the present invention may prevent severe health damage to a large population. For example, heart disease can therefore be noticed at an early stage.

A further advantage is that a multi-channel-ECG can be performed more frequently and that it does not require necessarily an operator. This can for example be beneficial for sportsmen- and women as well as patients and especially specific groups of patients.

In addition, using the presently preferred embodiment of the invention will reduce the time required to perform a multi-channel-ECG. The device of the invention performs a multi-channel-ECG between 15-30 seconds, where a conventional device requires several minutes. This enables performing a measurement and analysis more frequently. This will further improve accuracy.

A data processing element is configured to analyse the data and generate the multi-channel-ECG. The data processing element can be connected wired or wireless to the electrodes and/or processor. Data processing can be done in the handheld device and/or remotely.

In an embodiment of the invention the device comprises a screen and/or a memory. The screen can visualise for example the multi-channel-ECG and the memory can for example store the multi-channel-ECG. Both features will help to improve the understanding of the multi-channel-ECG. This enables display of the measurement results to both the user/patient and an expert.

A further advantage is the reduced complexity of the device as compared to conventional devices. The effects thereof are that the costs to manufacture are reduced, easier to maintain, and easier to operate.

In use, a number of electrodes, for example 2, 3, 4 or any other appropriate number, is operatively connected to the processor. Providing the housing with at least two electrodes has the advantage the multi-channel-ECG can be performed.

In a further preferred embodiment of the invention the processor is configured to record a 9-channel-ECG.

The 9-channel-ECG can provide a spatial image of the heart stimulus in two anatomical surfaces, a frontal surface and a transversal surface. As a result, this provides a more accurate analysis of the heart compared to a single-channel-ECG or ECG with less than 9 channels. In that respect, more channels for an ECG results in higher complexity.

In a further preferred embodiment of the invention the data processing element is a smartphone, wherein the smartphone is configured to process the data received from the electrodes and/or processor.

An advantage of such a data processing element is that communication with a doctor, nurse, emergency service, and the like is efficient since a smartphone can connect with internet and/or call an operator such as a doctor, nurse, emergency service, and the like. Furthermore, smartphones are readily available and can contain an operating system which can operate the device for recording a 9-channel-ECG.

Furthermore, smartphones comprise a gyroscope which are able to correct the housing and help the user to place it in the correct position.

In a further preferred embodiment of the invention the housing is provided with at least two electrodes. The housing is preferably provided with 2-12 electrodes, more preferably with 3-8 electrodes, even more preferably with 4-6 electrodes, most preferably with 4 electrodes.

Providing the housing with 4 electrodes has the advantage that the electrodes are easily configured, and that rapid diagnosis can be performed and that the diagnosis is sufficiently accurate.

In a presently preferred embodiment the at least two electrodes are adjustable using adjusting means, more specifically the electrodes are adjustable relative to the housing.

It will be understood that other types of appropriate adjusting means can also be envisaged in accordance to the invention.

Adjusting the electrodes will improve the connection between chest and device. This will result in and improved accuracy of the multi-channel-ECG. Furthermore, this enables providing a generic device that can be used by different people having different chest shapes.

For example, adjusting means comprise one or more of the following: spindles and/or ball joints and/or hinges and/or swivels and/or grooves.

In a further preferred embodiment of the invention the device comprises a contact surface which is provided with a shape which substantially corresponds with a chest.

The advantage of a shape which substantially corresponds with a chest is that a better quality of multi-channel-ECG is achieved. Therefore, fewer errors will occur and therefore, a higher accuracy in diagnostics will be achieved.

In a further preferred embodiment of the invention the chest shape of the device is adjusted to the end-user.

The advantage of a device having an adjusted chest shape is that an even better quality of multi-channel-ECG is achieved. Therefore, even fewer errors will occur and therefore, an even higher accuracy in diagnostics will be achieved.

A further advantage is a better fit to the chest of the end-user. This has the effect of an increased comfort for the end-user. As a further effect this may improve the willingness of the user to actually use the device according to the invention. This further increases the chance of early detection of any health problem.

Optionally, an adaptable surface or intermediate surface is applied. The advantage of an intermediate surface is the availability and lower costs compared to adaptable surfaces. An adaptable surface has the advantage of a further improvement of the fit to the chest of the end-user. Furthermore, a distinction can be made between surfaces used for, for example, but not limited to, male, female and children. An even better fit is achieved using a customised surface for specific patients.

In a presently preferred embodiment the shape is applied in combination with the adjusting means to even better achieve the contact between the device and the skin of the end-user.

In a further preferred embodiment of the invention the device is portable and further comprises an energy storage system.

The advantage of the device being portable is that it can be carried around easily. The effect is that the device can be used at all times in any suitable place. Providing the device with an energy storage system, it will be independent and does not have to rely on an external power supply. This will extend the physical range of the device. For example, the device can be taken outdoors by the end-user whilst doing exercises. Optionally, the device is provided with a solar panel to charge the energy storage system.

In a further preferred embodiment of the invention the electrode is made of and/or has a coating comprising silver and/or silver chloride and/or graphene and/or stainless steel and/or polymer and/or any other fast conduction material.

The coating provides for optimal contact between the skin of the end-user and electrode. This will result in effective diagnostics.

In a presently preferred embodiment, the electrode is made from silver. This will result in an efficient and effective monitoring of a heart stimulus.

It will be understood by the skilled person that when a polymer is used as coating in a presently embodiment of the device, the coating will be a fast conducting polymer. Furthermore, electrodes comprising a polymer and/or stainless steel coating have the advantage that these electrodes will not oxidise when exposed to air and/or water and have an extended life time compared to other types of coating. In a presently embodiment of the device the electrodes comprise stainless steel. Fast conduction materials are materials which have a relatively high conductivity.

In a further preferred embodiment of the invention the electrode has a round top and/or flat shape and/or rounded shape and/or cone shape. Preferably the electrode has a round top. The advantage of a round top is to improve the contact between the electrode and the skin. This will improve the quality of the multi-channel-ECG. It will be understood the top of the electrode can have other shapes, for example a flat shape and/or rounded shape and/or cone shape.

In a presently preferred embodiment of the device the electrodes are adjustable, include a round top and are applied in a shape which substantially corresponds with a chest.

In a further preferred embodiment of the invention the electrode comprises one or more contact structure enlarging means, such as contact structure enlarging dots.

Contact structure enlarging means can be for example, but are not limited to: contact structure enlarging dots, contact structure enlarging squares, contact structure enlarging grooves, contact structure enlarging triangles, contact structure enlarging rectangles.

The contact structure enlarging dots provide even further optimisation of contact between the skin of the end-user and electrode. This will result in even more effective diagnostics.

In a further preferred embodiment of the invention the electrode comprises a gyroscope and/or pressure sensor.

The gyroscope and/or pressure sensor provide even further optimisation of contact between the skin of the end-user and electrode. This will result in even more effective diagnostics.

It will be understood by the skilled person an electrode comprising a gyroscope and/or pressure sensor can be combined with any of the above described embodiments and/or features.

Said electrodes have a diameter in the range of 1.0 cm-2.5 cm, preferably in the range of 1.5 cm-2.5 cm, most preferably in the range of 1.5 cm-2.0 cm. Furthermore, said electrodes have a height of about 1.0 cm, preferably of about 0.8 cm, more preferably of about 0.5 cm, and most preferably of about 0.2 cm.

In a further preferred embodiment of the invention the back of the smartphone is operatively connected with the housing. The device for recording a multi-channel-ECG can be placed vertical near the bottom of the sternum. The device can be positioned at the same place each time the user is performing a multi-channel-ECG. An advantage of performing the multi-channel-ECG at the same place is that the diagrams can be compared. The smartphone can help to locate the right position.

In a further preferred embodiment of the invention the device comprises at least one filter, for example noise filter.

The at least one (noise) filter has the advantage that a 'clean' ECG-signal will be provided to software configured to process the obtained measurement. It will be understood by the skilled person a device comprising such a (noise) filter can be combined with any of the above described embodiments and/or features.

In a further preferred embodiment of the invention the device comprises a notification system to present an advice and/or warning, the notification system comprising:
- a transmitter configured for:
  - sending an e-mail; and/or
  - sending a notification to an app; and/or
  - sending a sms; and/or
  - calling a third party; and/or
  - generating a physical alarm.

The advantage of an implemented notification system is that an end-user will be notified when a measurement shows inconsistencies. This will result in earlier notice of heart problems.

Furthermore, the transmitter will act as an early warning system and will help to prevent health damage.

In a further preferred embodiment of the invention the device is capable to perform a number of scans at a sample rate in the range of 50 Hz-650 Hz, preferably in the range of 75 Hz-550 Hz, more preferably in the range of 100 Hz-450 Hz, even more preferably in the range of 125 Hz-350 Hz, and most preferably 250 Hz.

A larger number of scans will result in a higher accuracy of the multi-channel-ECG. A higher accuracy contributes to a better interpretation of the result and therefore fewer false negative or positive results.

The handheld device is easy to operate and to carry around by the end-user. Also, the device can be used to test humans and animals. For example, a veterinary can use this whilst on site. Due to the ease of use, animal owners can use one in order to prevent health damage to animals.

In a further preferred embodiment at least five channels are used to perform a multi-channel-ECG, preferably at least eight channels are used to perform a multi-channel-ECG, more preferably at least nine channels are used to perform a multi-channel-ECG, and most preferably at least ten channels are used to perform multi-channel-ECG.

The advantage of using multi-channel-ECG is that an accurate diagnosis is obtained.

Performing multi-channel-ECG gives results which can be used to determine the condition of the heart. The preferred embodiment can, for example, present an advice and/or warning.

The invention also relates to an electrode or set of electrodes for use in the device for recording multi-channel-ECG, the electrodes being capable with the device in one or more of the embodiments according to the invention.

The electrodes provide the same effects and advantages as those described for the device.

The invention also relates to electrodes in combination with a processing device. For example, the processing device comprises one or more of the following: computer, mobile device, tablet, mobile phone.

The invention further also relates to a method for recording a multi-channel-ECG, comprising the steps of:
- providing a device in an embodiment according to the invention and/or electrodes according to the invention;
- performing a measurement using the electrodes; and
- adjusting and/or presenting and/or analysing of the measurement.

The method provides the same effects and advantages as those described for the device and/or electrode(s).

More specifically, the method enables the implementation of the electrodes inside the patient. Therefore, a more accurate multi-channel-ECG will be obtained and can be continuously performed. This will result in a more accurate diagnose and early heart disease can be detected.

The method can be applied at any place and time. Furthermore, the method is easy applicable and can therefore be performed by an end-user.

The method will act as an early warning system and may prevent severe health damage.

Figure 1:
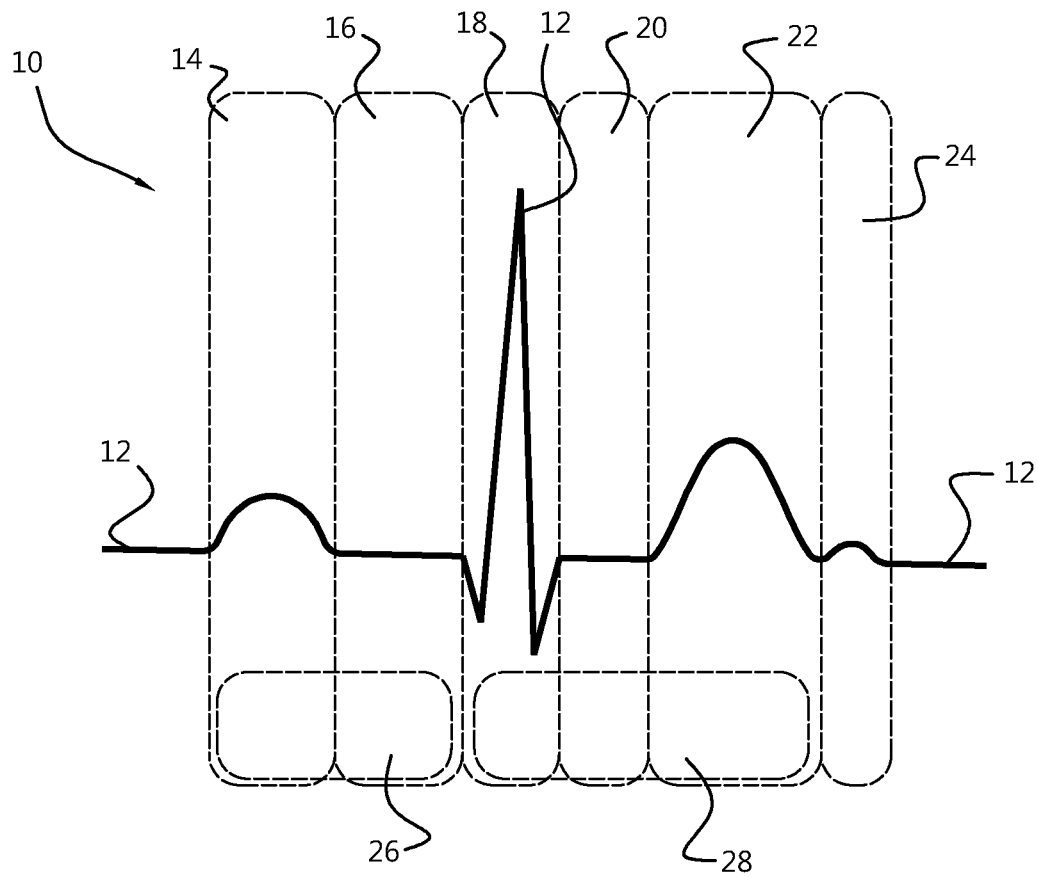
Figure 2:
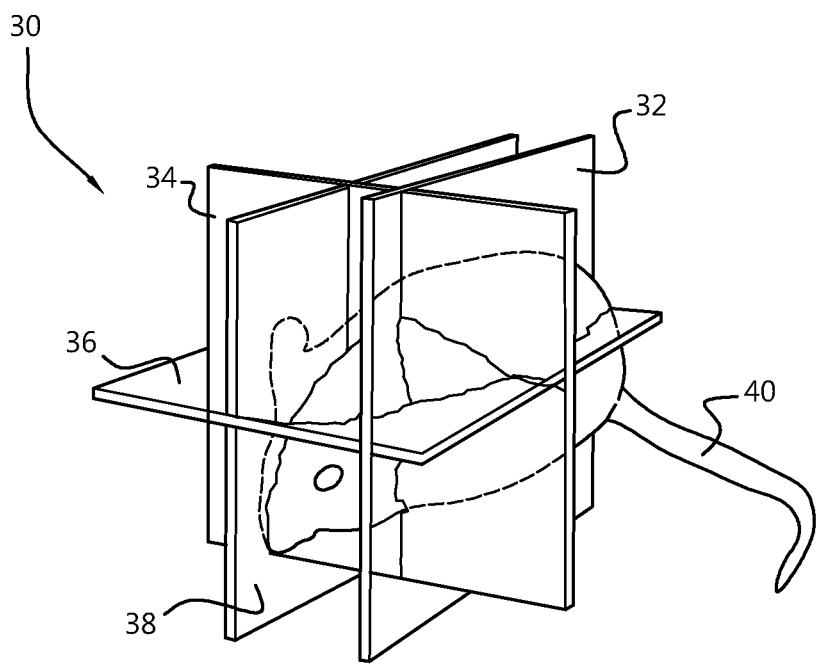
Figure 3:
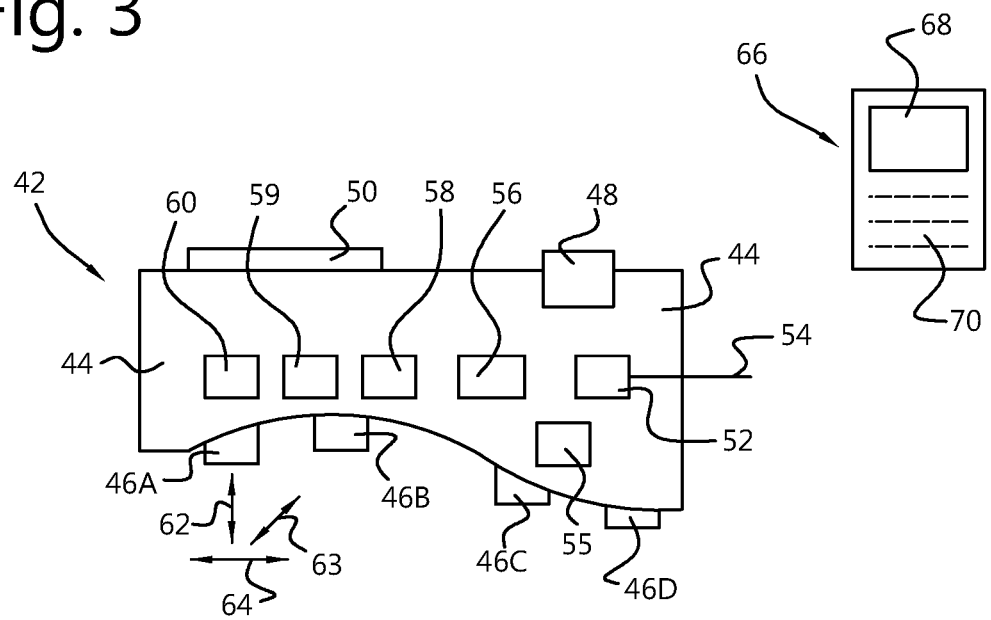
Figure 4:
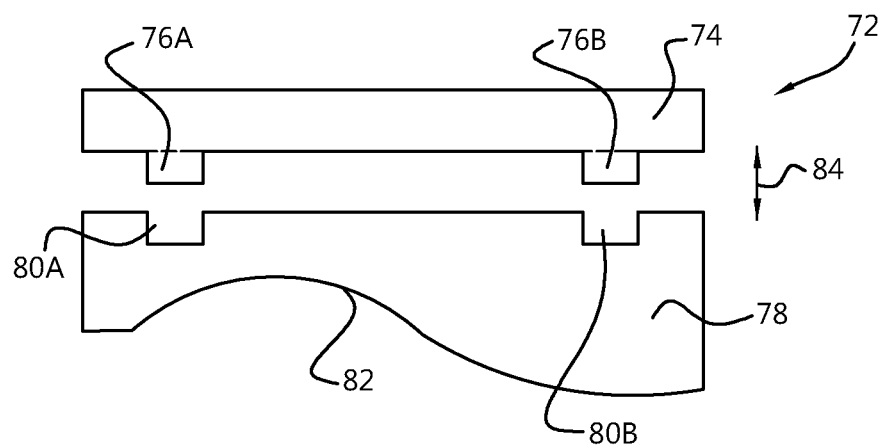
Figure 5:
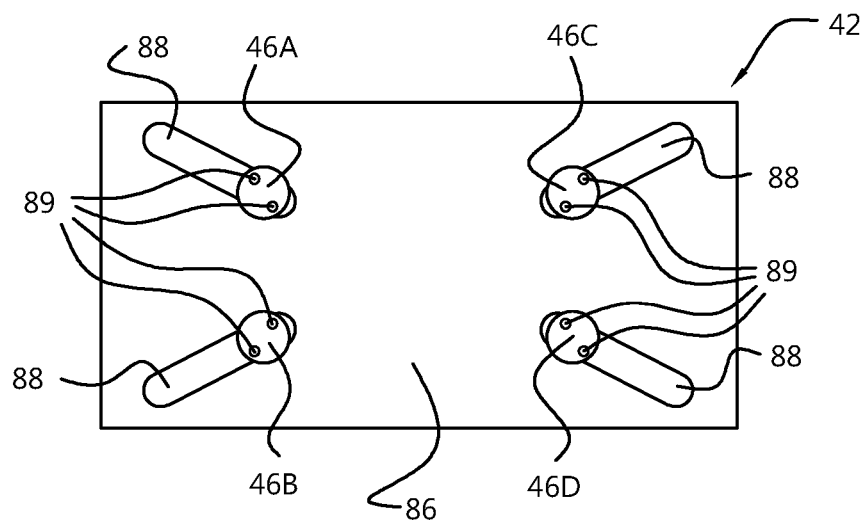
Figure 6:
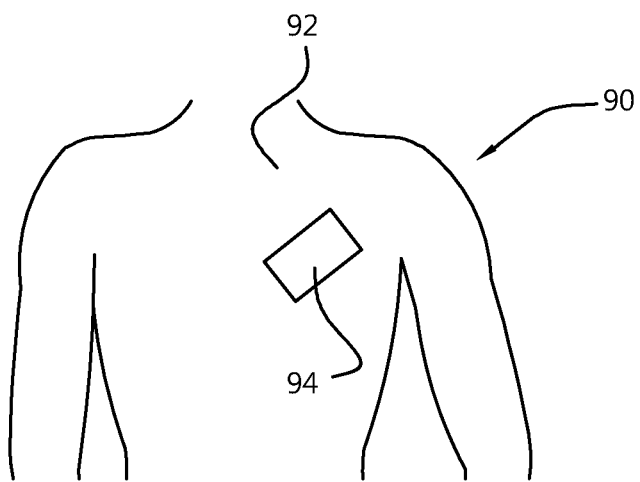

Further advantages, features and details of the invention are elucidated on the basis of preferred embodiments thereof, wherein reference is made to the accompanying drawings, in which:

FIG. 1 shows an action potential of a heart on a ECG;
FIG. 2 shows different anatomical surfaces of the heart;
FIG. 3 shows a medical device for multi-channel-ECG;
FIG. 4 shows a medical device for multi-channel-ECG which can be connected to a data processing element;
FIG. 5 shows a configuration of electrodes;
FIG. 6 shows a position of the handheld medical device on the chest;
FIG. 7 shows a 9-channel-ECG registered in two anatomical surfaces, frontal and transversal; and
FIG. 8 shows a 9-channel-ECG when ischemia is detected.

It will be understood that the terms anatomical surface and anatomical plane are interchangeable.

Action potential 10 (FIG. 1) shows a P-QRS-T complex 12 with P wave 14, PR segment 16, QRS complex 18, ST segment 20, T wave 22, and U wave 24. P wave 14 and PR segment 16 together form PR interval 26. QRS complex 18, ST segment 20 and T wave 22 together form QT interval 28.

Orientation of heart 30 (FIG. 2) shows different anatomical surfaces of the heart. The surfaces are defined as sagittal surface 32, transversal surface 34, frontal surface 36 and median surface 38.

Medical device 42 (FIG. 3) comprises housing 44. In the illustrated embodiment housing 44 holds four electrodes. These are electrodes 46A, 46B, 46C and 46D. Input is provided by input module 48 and connection module 52 can connect to external device 66 using connector 54. Housing 44 further comprises energy storage system 55, processor 56, memory 58, notification system 59 and adjustment means 60. Adjustment means 60 can adjust and/or move electrodes 46A and/or 46B and/or 46C and/or 46D preferably in all directions, for example in height direction 62 and/or width direction 63 and/or length direction 64.

Furthermore, in the illustrated embodiment external device 66 comprises screen 68 and input module 70.

Connection 54 can, for example, but is not limited to, be a cable and/or a wire and/or WiFi and/or Blue Tooth and/or infrared.

Energy storage system 55 can, for example, but is not limited to, be and/or a battery and/or super capacitor and/or accu and/or storage cell and/or fuel cell.

Adjustment means 60 can, for example, but are not limited to, be a spindle and/or a groove and/or ball joints and/or hinges and/or swivels.

In a preferred embodiment, all electrodes are fitted with adjustment means.

External device 66 can be for example, but is not limited to, a computer and/or a tablet and/or a mobile phone and/or a server.

Medical device 72 (FIG. 4) comprises a processing module 74 and a scanning module 78.

Processing module 74 comprises connection element 76A and 76B. Scanning module 78 comprises connection element 80A and 80B. The assembly of connection element 76A and 76B engage with respectively connection element 80A and 80B. Processing module 74 and scanning module 78 can be separated 84.

In a preferred embodiment medical device 72 shows scanning module 78 having a chest shape 82.

FIG. 5 shows surface 86 of medical device 42 which connects with the skin of the end-user. Surface 86 holds grooves 88 to adjust electrodes 46A, 46B, 46C and 46D. Electrodes 46A, 46B, 46C and 46D having contact structure enlarging dots 89.

Similar applies to scanning module 78.

Body 90 (FIG. 6) shows the placement of medical device 94 on chest 92. Medical device 94 can be medical device 42 (FIG. 3) or medical device 72 (FIG. 4) or another embodiment according to the invention.

The embodiment of the above mentioned medical device 94 is easy and straightforward to use. The electrodes of the device are pushed against the chest, preferably at the bottom of the sternum in a vertical orientation. The electrodes can contact the skin free of gel or conduction solution. Furthermore, the electrodes are attached to the medical device.

FIG. 7 shows a 9-channel-ECG, wherein four electrodes are used to provide an ECG in two anatomical surfaces, the frontal surface and transversal surface. Providing such an ECG results in a spatial image of the heart stimulus. The 9-channel-ECG is of a healthy human, wherein channels I, II, III, aVR, aVL, aVF provides diagrams in the frontal surface and channels V1, V2 and V3 provides diagrams in the transversal surface. The X-axis is defined in 25 mm/s and the Y-axis is defined in 10.0 mm/mV.

FIG. 8 shows a 9-channel-ECG, wherein four electrodes are used to provide an ECG in two anatomical surfaces, the frontal surface and the transversal surface. It becomes clear that the biphasic T-waves indicate that ischemia is present. The 9-channel-ECG is of a pig with induced ischemia, wherein channels I, II, III, aVR, aVL, aVF provides diagrams in the frontal surface and channels V1, V2 and V3 provides diagrams in the transversal surface. The X-axis is defined in 25 mm/s and the Y-axis is defined in 5.0 mm/mV.

It will be understood that the anatomical surface, frontal surface and transversal surface also refers to anatomical plane, frontal plane and transversal plane respectively.

In use, the device can be operated by the end-user, which may be a patient or another user that is not skilled in medical science. Naturally, the device may also be used by skilled medical personnel. The end-user has to press the device against his or her chest. Preferably, the device has a shape that conforms with the shape of the chest, such that the device exactly follows the contour of the chest to which it is held. Subsequently, the end-user activates the device, which performs a measurement and provides an ECG. The device is, during each of the consecutive measurements, placed at the same location against the chest of the end-user. Preferably, this place is at the bottom of the sternum, wherein the device is placed vertically on the sternum. This is made easier when the shape of the device conforms with the shape of the chest of the end-user. However, in any case, slight deviations in the position of the device on the chest or in the position of the chest itself (due to for example breathing) may be compensated by gyroscopes that are built into the device. As a result, the consecutively made ECGs are easily comparable and provide a timeline of ECGs.

In a specific example, the device is a smartphone or similar device that is operated by the end-user. The end-user places the rear side of the smartphone against his or her chest. The rear side of the smartphone has a shape that conforms with the shape of the chest and thus exactly follows the contour of the chest to which it is held. Due to the fact that the rear side of the smartphone has a surface conforming to the chest contour, placing the smartphone at the same location for each time of use is easy. Moreover, the built-in gyroscopes of the smartphone correct for slight deviations in the measuring position of the smartphone at the chest or in the position of the chest itself (due to for example breathing).

Optionally, the user may adjust electrodes, use an intermediate surface and/or adapter to improve the contact between electrodes and the skin.

The output can be analysed by the device and/or end-user. The output can be automatically send to, for example but not limited to, a hospital and/or GP and/or ambulance service.

The present invention is by no means limited to the above described and preferred embodiments thereof. The rights sought are defined by the following claims within the scope of which many modifications can be envisaged.

The invention claimed is:

1. A device for recording a multi-channel-ECG, comprising:
   a housing;
   a processor positioned in the housing and configured to record the multi-channel-ECG;
   at least two electrodes configured to be operatively connected with the processor, wherein the at least two electrodes are provided on the housing;
   a data processing element; and
   a connection module configured to connect the at least two electrodes and/or processor with the data processing element,
   wherein the device is configured to be handheld; and
   wherein the device further comprises adjusting means configured to adjust and move the positions of the at least two electrodes relative to the housing, the adjusting means including elongated grooves to allow shifting of the at least two electrodes along a surface of the housing.

2. The device according to claim 1, wherein the at least two electrodes comprise at least four electrodes, and wherein the multi-channel-ECG is a 9-channel-ECG.

3. The device according to claim 1, wherein the data processing element is a smartphone and wherein the connection module is operatively connectable with the smartphone.

4. The device according to claim 3, wherein the at least two electrodes comprise one or more contact structure enlarging means, further comprising a contact surface which has a shape, and wherein the shape of the contact surface is adjustable to conform to a chest shape of the end-user.

5. The device according to claim 4, wherein the device is configured to perform a number of the multi-channel ECG scans of a patient at a sample rate in the range of 50 Hz-650 Hz.

6. The device according to claim 1, wherein the at least two electrodes comprise four electrodes.

7. The device according to claim 1, wherein the adjusting means are configured to adjust and/or move the at least two electrodes in a height direction of the housing and/or a width direction of the housing and/or a length direction of the housing.

8. The device according to claim 1, further comprising a contact surface that is connected to the housing and has a shape.

9. The device according to claim 8, wherein the shape of the contact surface is adjustable to conform to a chest shape of the end-user.

10. The device according to claim 1, wherein the device is portable and further comprises an energy storage system positioned within the housing.

11. The device according to claim 10, further comprising a screen operatively connected to the housing.

12. The device according to claim 1, wherein the at least two electrodes are made of and/or have a coating comprising silver and/or silver chloride and/or graphene and/or stainless steel and/or polymer and/or any other fast conduction material.

13. The device according to claim 1, wherein the at least two electrodes have a round top and/or flat shape and/or rounded shape and/or cone shape.

14. The device according to claim 1, wherein the at least two electrodes comprise one or more contact structure enlarging means.

15. The device according to claim 1, further comprising a notification system positioned in the housing to present an advice and/or warning, the notification system comprising a transmitter configured for at least one of sending an e-mail, sending a notification to an app, sending an sms, calling a third party, and generating a physical alarm.

16. The device according to claim 1, wherein the device is configured to perform a number of the multi-channel ECG scans of a patient at a sample rate in the range of 50 Hz-650 Hz.

17. A method for recording a multi-channel-ECG, comprising the steps of:

providing a device for recording a multi-channel-ECG, the device comprising:
a housing;
a processor positioned within the housing and configured to record the multi-channel-ECG;
at least two electrodes configured to be operatively connected with the processor, wherein the at least two electrodes are provided on the housing;
a data processing element; and
a connection module configured to connect the at least two electrodes and/or processor with the data processing element,
wherein the device is configured to be handheld, and the device further includes adjustment means for adjusting and moving the position of the electrodes relative to the housing, the adjusting means including elongated grooves to allow shifting of the at least two electrodes along a surface of the housing;
performing a measurement using the electrodes; and
adjusting and/or presenting and/or analysing the measurement.

18. The method according to claim 17, further comprising applying the device and/or the electrodes using a contact surface.

* * * * *